United States Patent
Kohls et al.

(10) Patent No.: US 10,843,999 B2
(45) Date of Patent: Nov. 24, 2020

(54) PROCESS FOR PREPARING PENTENOATE

(71) Applicant: PATHEON AUSTRIA GMBH & CO KG, Linz (AT)

(72) Inventors: Paul Kohls, Linz (AT); Peter Pöchlauer, Linz (AT); Stefan Steinhofer, Enns (AT); Christian Schuster, Kremsmünster (AT)

(73) Assignee: Patheon Austria GmbH & Co KG, Linz (AU)

( * ) Notice: Subject to any disclaimer, the term of this patent is extended or adjusted under 35 U.S.C. 154(b) by 0 days.

(21) Appl. No.: 16/484,364

(22) PCT Filed: Feb. 12, 2018

(86) PCT No.: PCT/EP2018/053434
§ 371 (c)(1),
(2) Date: Aug. 7, 2019

(87) PCT Pub. No.: WO2018/146306
PCT Pub. Date: Aug. 16, 2018

(65) Prior Publication Data
US 2020/0002263 A1    Jan. 2, 2020

(30) Foreign Application Priority Data
Feb. 13, 2017  (EP) .................................... 17155927

(51) Int. Cl.
*C07C 67/343*  (2006.01)
*C07C 69/732*  (2006.01)

(52) U.S. Cl.
CPC .......... *C07C 67/343* (2013.01); *C07C 69/732* (2013.01)

(58) Field of Classification Search
CPC .................................................. C07C 67/343
See application file for complete search history.

(56) References Cited

U.S. PATENT DOCUMENTS

| | | | |
|---|---|---|---|
| 2012/0073187 A1* | 3/2012 | Mancini | B01J 31/0212 44/398 |
| 2013/0217909 A1 | 8/2013 | Pariente et al. | |

(Continued)

OTHER PUBLICATIONS

Zibuck, R. et al., A new preparation of ethyl 3-oxo-4-pentenoate: A useful annelating reagent, 1989, Journal of Organic Chemistry, vol. 54, No. 19, pp. 4717-4719 (Year: 1989).*

(Continued)

*Primary Examiner* — Yate' K Cutliff
(74) *Attorney, Agent, or Firm* — Raymond G. Arner; Pierce Atwood LLP

(57) ABSTRACT

The invention pertains to a process for preparing a compound of formula (1)

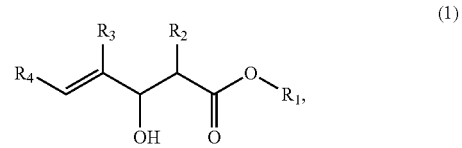

wherein $R_1$ is independently chosen from $C_1$-$C_6$ alkyl, cycloalkyl, aralkyl and aryl, and $R_2$, $R_3$ and $R_4$ are independently chosen from hydrogen and $C_1$-$C_6$ alkyl, cycloalkyl, aralkyl and aryl;
which process comprises the steps of:

(Continued)

a) contacting a compound of formula (2)

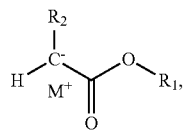

(2)

wherein $R_1$ and $R_2$ are as above and $M^+$ is a monovalent metal ion,
with a compound of formula (3)

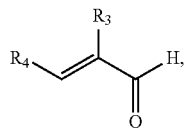

(3)

wherein $R_3$ and $R_4$ are as above,
to form a compound of formula (4)

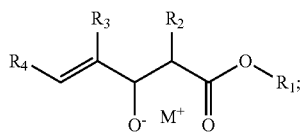

(4)

and
b) followed by contacting the compound of formula (4) with an acid to give a compound of formula (1),
wherein step (a) and/or step (b) are conducted in continuous mode.

10 Claims, 1 Drawing Sheet

(56) References Cited

U.S. PATENT DOCUMENTS

| | | | | |
|---|---|---|---|---|
| 2013/0267719 | A1* | 10/2013 | Mikochik | C07D 307/68 |
| | | | | 549/484 |
| 2014/0051869 | A1* | 2/2014 | McCormack | C07C 67/343 |
| | | | | 549/375 |
| 2015/0087861 | A1* | 3/2015 | Devaux | C07C 45/52 |
| | | | | 562/532 |

OTHER PUBLICATIONS

International Search Report for International application No. PCT/EP2018/053434 dated Mar. 12, 2018.
Zibuck et al., "A New preparation of Ethyl 3-0xo-4-pentenoate", Journal of Organic Chemistry, vol. 54, Dec. 31, 1989, pp. 4717-4719.
Official European Search Report dated Jul. 28, 2017 in European Application No. 17155927.1, 7 pages.
Zibuck et al., "A New Preparation of Ethyl 3-Oxo-4-Penenoate", Journal of Organic Chemistry, vol. 54, Dec. 31, 1989 (Dec. 31, 1989), pp. 4727-4729.

* cited by examiner

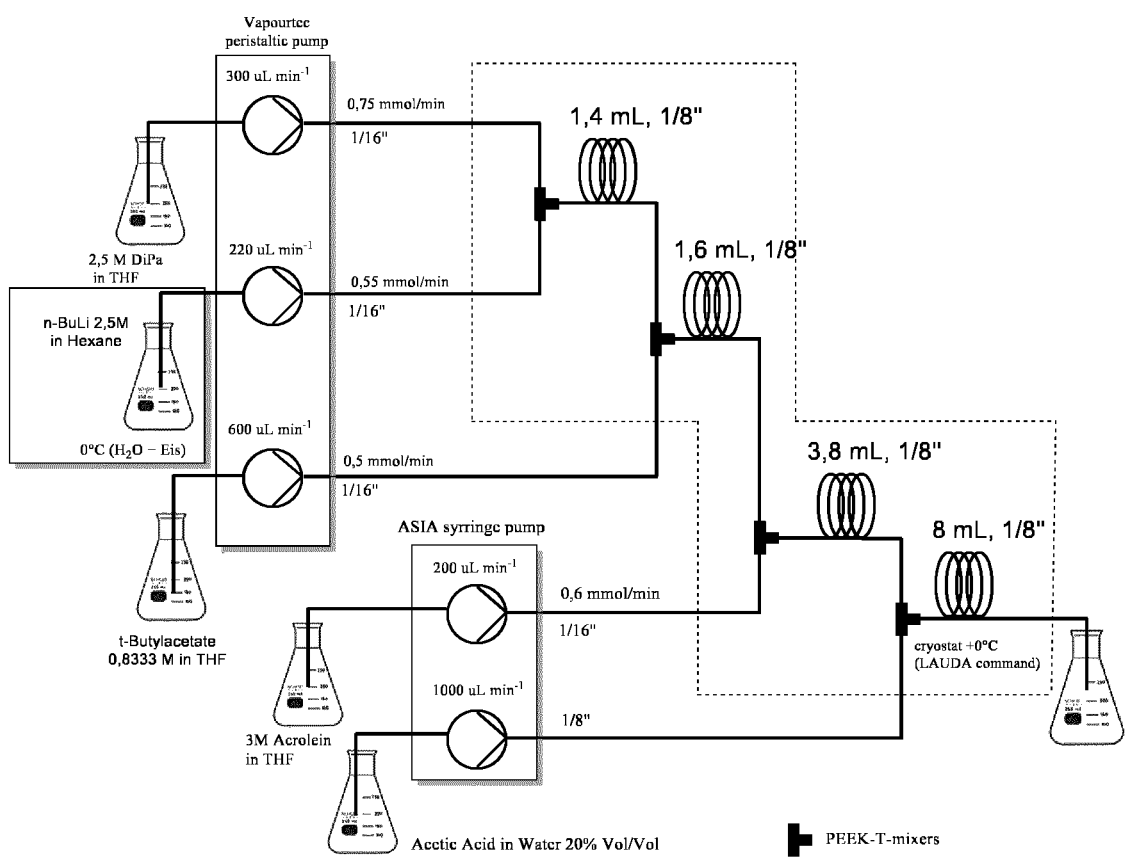

PROCESS FOR PREPARING PENTENOATE

CROSS REFERENCE TO RELATED APPLICATIONS

This application is a U.S. National Stage of PCT International Application No. PCT/EP2018/053434, filed Feb. 12, 2018, which claims priority to European Patent Application No. 17155927.1, filed Feb. 13, 2017, the entire contents of which is incorporated herein by reference.

The present invention relates to processes for preparing pentenoate and pentenoate-like compounds. The invention further provides a process for preparing propenals.

Synthetic routes for the preparation of pentenoate and pentenoate-like compounds are known in the art. Kelly et al (in Tetrahedron Letters, vol. 40, Iss. 16 (1999), pp. 3251-3254) discloses the synthesis of pentenoate by the reaction of bromo acetate derivatives and propenal derivatives in the presence of a Zinc-based catalyst. A further synthesis uses the condensation of acetate derivatives as described by Dewi-Wuelfling et al. (in Synlett, nb. 3 (2006), pp. 487-489). These reactions are exothermic and is consequently difficult to control and obtain high yields. Moreover, propenals, in particular acrolein, have a tendency to polymerize, rendering these compounds difficult to store and/or transport without substantial deterioration of the required propenal. Using such propenals to produce pentenoate or pentenoate-like compounds leads to an even lower yield and presence of (more) undesirable by-products.

The objective of the present invention is to provide a novel process as well as an improved process to prepare pentenoate and pentenoate-like compounds.

The present invention pertains to a process for preparing a compound of formula (1)

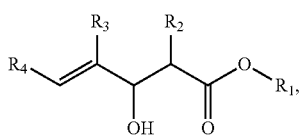

wherein $R_1$ is independently chosen from $C_1$-$C_6$ alkyl, cycloalkyl, aralkyl and aryl, and $R_2$, $R_3$ and $R_4$ are independently chosen from hydrogen and $C_1$-$C_6$ alkyl, cycloalkyl, aralkyl and aryl;

which process comprises the steps of:

a) contacting a compound of formula (2)

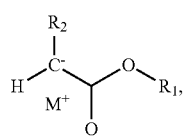

wherein $R_1$ and $R_2$ are as above and $M^+$ is a monovalent metal ion, with a compound of formula (3)

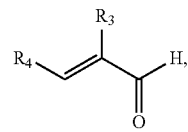

wherein $R_3$ and $R_4$ are as above, to form a compound of formula (4)

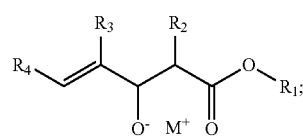

and b) followed by contacting the compound of formula (4) with an acid to give a compound of formula (1), wherein step (a) and/or step (b) are conducted in continuous mode.

The process has the advantage that it is safe and the compound of formula (1) can be prepared with a good yield and good selectivity. By conducting steps (a) and/or (b) in continuous mode, and in particular when these steps are conducted in a microreactor or tube reactor, the process conditions can be controlled better and safety is considerably improved. A further advantage is that generally these process steps can be conducted at a higher temperature compared to batch-like processes that generally require cryogenic temperatures. Moreover, the productivity of the process of the invention is generally higher.

The substituents $R_1$, $R_2$, $R_3$ and $R_4$ are present in any one of the compounds (1) to (4) wherein $R_1$ is independently chosen from $C_1$-$C_6$ alkyl, cycloalkyl, aralkyl and aryl, and $R_2$, $R_3$ and $R_4$ are independently chosen from hydrogen and $C_1$-$C_6$ alkyl, cycloalkyl, aralkyl and aryl. These substituents can be the same or different. Preferably, the substituents $R_1$, $R_2$, $R_3$ and $R_4$ are hydrogen and/or $C_1$-$C_4$ alkyl. Even more preferably the substituents $R_1$ is alkyl, preferably ethyl, sec-butyl or tert-butyl and $R_2$, $R_3$ and $R_4$ are hydrogen or methyl. Even more preferably the substituents $R_1$ is alkyl, preferably ethyl, sec-butyl or tert-butyl and $R_2$, $R_3$ and $R_4$ are hydrogen.

$M^+$ represents a monovalent metal ion. The metal ion $M+$ can be any metal ion that can be suitably used in the compounds of formulae (2) and (4). Examples of suitable metal ions include $Na^+$, $Li^+$ and $K^+$. Preferably, the metal ion is $Li^+$ and $K^+$. Most preferably, the metal ion is $Li^+$.

In step (a) of the process of the invention the compounds of formulae (2) and (3) are contacted to form a compound of formula (4). Preferably, the compound of formula (2) is tert-butyl acetate, ethyl acetate and sec butyl acetate and the compound of formula (3) is acrolein, 2-methylpropen-2-al and 4-methylbuten-2-al. More preferably, the compound of formula (2) is tert-butyl acetate and the compound of formula (3) is acrolein.

In one embodiment of the invention, the molar ratio of the compound of formula (2) and the compound of formula (3) is at least 0.1, preferably at least 0.5, more preferably at least 0.8 and most preferably at least 1, and generally at most 10, preferably at most 8, more preferably at most 6 and most preferably at most 5.

Optionally, a catalyst is present during this process step. Examples of suitable catalysts include chiral catalysts known in the art.

In one embodiment of the invention, the molar ratio of the catalyst and the compound of formula (2) is at least 0.001, preferably at least 0.002, more preferably at least 0.005 and most preferably at least 0.01, and generally at most 1, preferably at most 0.5, more preferably at most 0.2 and most preferably at most 0.1.

Optionally, a solvent is present during this process step. Examples of suitable solvents include alkanes such as pentane, hexane and heptane; and ethers such as tert-butyl methyl ether and tetrahydrofuran (THF). Also a combination of two or more solvents is contemplated. Preferably, the solvent is selected from alkanes, in particular hexane and heptane, and THF. Most preferably, the solvent is THF.

In one embodiment, the reaction mixture comprises the solvent in an amount of at least 50% by weight (wt %), based on the total weight of the reaction mixture. Preferably, the solvent is present in an amount of at least 55 wt %, more preferably at least 60 wt %, even more preferably at least 65 wt % and most preferably at least 70 wt %, and preferably at most 99 wt %, more preferably at most 95 wt %, even more preferably at most 90 wt % and most preferably at most 85 wt %, based on the total weight of the reaction mixture. The reaction mixture includes all ingredients that are necessary to convert the compounds of formulae (2) and (3) into the compound of formula (4), i.e. it includes the compounds of formulae (2) and (3), the (optional) catalyst, the (optional) solvent and any other ingredient present.

In one aspect, this process step is conducted at a temperature of at least −100° C., preferably at least −50° C., more preferably at least −20° C. and most preferably at least −10° C., and preferably at most 30° C., more preferably at most 20° C. and most preferably at most 10° C.

In step (b) of the process of the invention the compound of formula (4) is contacted with an acid to form a compound of formula (1). The acid can be any acid suitable in the process of the invention. Examples of such acids include sulfuric acid, acetic acid, citric acid, hydrogen chloride, p-toluene sulfonic acid (pTsOH) and methane sulfonic acid. Preferably, the acid is citric acid and acetic acid. Most preferred, the acid is acetic acid.

In one embodiment of the invention, the molar ratio of the acid and the compound of formula (4) is at least 0.1, preferably at least 0.3, more preferably at least 0.5 and most preferably at least 1.0, and generally at most 5, preferably at most 2, more preferably at most 1.5 and most preferably at most 1.1.

Optionally, a solvent is present during this step of the process. Examples of suitable solvents include alcohols such as methanol, ethanol or isopropanol; alkylene glycols such as ethylene glycol and propylene glycol; and water. Also a combination of two or more solvents is contemplated. Preferably, the solvent is water or an alcohol, in particular methanol, ethanol and isopropanol. Most preferably, the solvent is water or methanol.

In one embodiment, the reaction mixture comprises the solvent in an amount of at least 50% by weight (wt %), based on the total weight of the reaction mixture. Preferably, the solvent is present in an amount of at least 55 wt %, more preferably at least 60 wt %, even more preferably at least 65 wt % and most preferably at least 70 wt %, and preferably at most 99 wt %, more preferably at most 95 wt %, even more preferably at most 90 wt % and most preferably at most 85 wt %, based on the total weight of the reaction mixture. The reaction mixture includes all ingredients that are necessary to convert the compound of formula (4) into the compound of formula (1), i.e. it includes the compound of formula (4), the acid, the (optional) solvent and any other ingredient present.

In one aspect, this process step is conducted at a temperature of at least −40° C., preferably at least −20° C. and most preferably at least −10° C., and preferably at most 50° C., more preferably at most 20° C. and most preferably at most 10° C.

The process of the invention may further comprise the step, wherein the compound of formula (2) is formed by the step of:

(c) contacting a compound of formula (5)

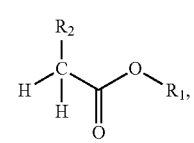

(5)

with a base.

Preferably, this step (c) of the process may further be conducted in continuous mode. The advantage of conducting this step in continuous mode is that the formed compound of formula (2) can be fed continuously into step (a) of the process of the invention described above without the need for a separation and/or purification step, or storage and/or transport of the compound of formula (2).

The compound of formula (5) is contacted with a base to form a compound of formula (2). The compound of formula (2) can subsequently be used in step (a) of the process of the invention to form a compound of formula (4). The base can be any base that can be suitably used in the process of the present invention. Examples of such bases include lithium diisopropyl amide, potassium diisopropyl amide, potassium tert-butoxide, sodium tert-butoxide, lithium hexamethyl disilazane and potassium hexamethyl disilazane. Preferably, the base is selected from lithium diisopropyl amide and lithium hexamethyl disilazane. Most preferably, the base is lithium diisopropyl amide. It is noted that lithium diisopropyl amide can be added to the reaction mixture as such or can be formed in situ. In a preferred embodiment, the combination of diisoproyl amine and n-butyl lithium are added to the reaction mixture to form lithium diisopropyl amide in situ.

In one embodiment of the invention, the molar ratio of the base and the compound of formula (5) is at least 0.1, preferably at least 0.5, more preferably at least 0.8 and most preferably at least 1, and generally at most 10, preferably at most 8, more preferably at most 6 and most preferably at most 5.

Optionally, a catalyst is present during this process step. In one embodiment of the invention, the catalyst is a non-racemic catalyst. Examples of suitable catalysts include chiral bis(oxazoline) copper(II) complexes and chiral amino acid-derived catalysts such as catalysts derived from L-proline and 5,5-dimethyl thiazolidinium-4-caroxylate (DMTC).

In one embodiment of the invention, the molar ratio of the catalyst and the compound of formula (5) is at least 0.001, preferably at least 0.002, more preferably at least 0.005 and most preferably at least 0.01, and generally at most 1, preferably at most 0.5, more preferably at most 0.2 and most preferably at most 0.1.

Optionally, a solvent is present during this process step. Examples of suitable solvents include alkanes such as pentane, hexane and heptane; and ethers such as tert-butyl methyl ether and tetrahydrofuran (THF). Also a combination of two or more solvents is contemplated. Preferably, the solvent is selected from alkanes, in particular hexane and heptane, and THF. Most preferably, the solvent is THF.

In one embodiment, the reaction mixture comprises the solvent in an amount of at least 50% by weight (wt %), based on the total weight of the reaction mixture. Preferably, the solvent is present in an amount of at least 55 wt %, more preferably at least 60 wt %, even more preferably at least 65 wt % and most preferably at least 70 wt %, and preferably at most 99 wt %, more preferably at most 95 wt %, even more preferably at most 90 wt % and most preferably at most 85 wt %, based on the total weight of the reaction mixture. The reaction mixture includes all ingredients that are necessary to convert the compound of formula (5) into the compound of formula (2), i.e. it includes the compound of formula (5), the base, the (optional) solvent and any other ingredient present.

In one aspect, this process step is conducted at a temperature of at least −100° C., preferably at least −50° C., more preferably at least −20° C. and most preferably at least −10° C., and preferably at most 30° C., more preferably at most 20° C. and most preferably at most 10° C.

The process of the invention may alternatively or additionally comprise the step wherein the compound of formula (3) is formed by the step of:

(d) dehydration of a compound of formula (6)

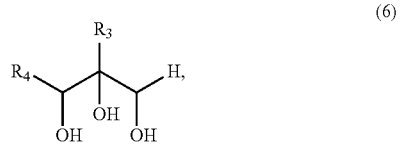

(6)

in the presence of an acid catalyst.

Preferably, this step (c) of the process may further be conducted in continuous mode. The advantage of conducting this step in continuous mode is that the formed compound of formula (3) can be fed continuously into step (a) of the process of the invention described above without the need for storage and/or transport of the compound of formula (3). Compounds of formula (3) such as acrolein are generally hazardous and toxic, rendering their transport and storage to be costly. Moreover, such storage and transport increases the presence of polymerization products of the compound of formula (3), which in turn decreases the yield of the process, and requires a purification step. The immediate and/or continuous use of the compound of formula (3) into step (a) of the process overcomes these issues, and moreover allows for better process control and increase the process safety and stability.

The compound of formula (6) is contacted with an acid catalyst capable of dehydrating the compound of formula (6) to form a compound of formula (3). The compound of formula (3) can subsequently be used in step (a) of the process of the invention to form a compound of formula (4). The acid catalyst may be any acid that can be suitably used in the process of the present invention. Examples of such acids include sulfuric acid, phosphoric acid, potassium bisulfate/potassium sulfate mixture, hydrogen chloride, p-toluene sulfonic acid (pTsOH) and methane sulfonic acid. Preferably, the acid is sulfuric acid.

In one embodiment of the invention, the molar ratio of the acid catalyst and the compound of formula (6) is at least 0.001, preferably at least 0.003, more preferably at least 0.005 and most preferably at least 0.01, and generally at most 1, preferably at most 0.5, more preferably at most 0.3 and most preferably at most 0.2.

Optionally, a solvent is present during this step of the process. Examples of suitable solvents include alcohols, in particular alcohols having a boiling point above 180° C., preferably above 200° C., such as alkylene glycols like tetraethylene glycol, polyethylene glycols, polypropylene glycols and ethers such as diphenyl ether. Also a combination of two or more solvents is contemplated. Preferably, the solvent is an alcohol, in particular polyethylene glycol.

On one embodiment, the reaction mixture comprises the solvent in an amount of at least 1% by weight (wt %), based on the total weight of the reaction mixture. Preferably, the solvent is present in an amount of at least 3 wt %, more preferably at least 5 wt %, even more preferably at least 8 wt % and most preferably at least 10 wt %, and preferably at most 50 wt %, more preferably at most 30 wt %, even more preferably at most 25 wt % and most preferably at most 20 wt %, based on the total weight of the reaction mixture. The reaction mixture includes all ingredients that are necessary to convert the compound of formula (6) into the compound of formula (3), i.e. it includes the compound of formula (6), the acid, the (optional) solvent and any other ingredient present.

In one aspect, this process step is conducted at a temperature of at least 150° C., preferably at least 170° C. and most preferably at least 190° C., and preferably at most 250° C., more preferably at most 230° C. and most preferably at most 220° C.

The invention further pertains to a process for preparing the compound of formula (2)

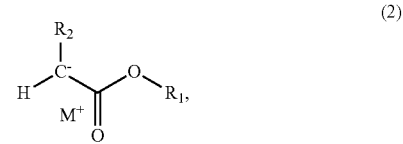

(2)

wherein $R_1$ is independently chosen from $C_1$-$C_6$ alkyl, cycloalkyl, aralkyl and aryl, and $R_2$ is independently chosen from hydrogen and $C_1$-$C_6$ alkyl, cycloalkyl, aralkyl and aryl; and wherein the process comprises the step of (a) contacting a compound of formula (5)

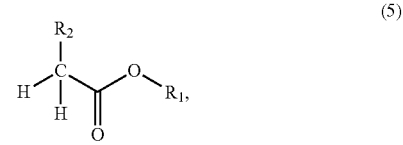

(5)

with a base,
wherein step (a) is conducted in continuous mode.
The reactants and amounts are as described above.
The invention further pertains to a process for preparing the compound of formula (3)

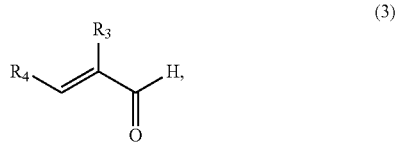

wherein $R_3$ and $R_4$ are independently chosen from hydrogen and $C_1$-$C_6$ alkyl, cycloalkyl, aralkyl and aryl; and wherein the process comprises the step of:
(a) dehydration of a compound of formula (6)

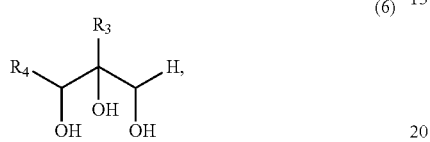

in the presence of an acid catalyst: and
wherein step (a) is conducted in continuous mode.

Preferably, the compound of formula (6) is glycerol and the compound of formula (3) is acrolein. The reactants and amounts are as described above.

The processes of the invention are preferably conducted in continuous mode. Suitable continuous reactors include continuously operated stirred tank reactors, micro- or millireactors. Each of these differs only from conventional size reactors in the dimensions and constructions of the reaction channel structures. A micro- or millireactor is a miniaturized reactor with characteristic dimensions (channel width and depth, or plate width) in micrometers (microreactor) to millimeters (millireactor). The characteristic dimensions are the dimensions perpendicular to the flow of the reaction mixture through the microreactor. The characteristic dimensions are for example from 0.1 mm to 20 mm; typically from 1 to 10 mm, for example 2 to 5 mm. In one embodiment, the process of the invention can be conducted in a micro- or millireactor, wherein the conversion of the compound of formula (6) to a compound of formula (3) is conducted in a continuously operated stirred tank reactor.

Preferably, a micro- or millireactor is defined as a reactor having a channel with a hydraulic diameter of 20 mm or less. The hydraulic diameter Dh is defined as 4A/U, wherein A is the cross sectional area of the reactor channel and U is the perimeter of said cross section. Such reactors are described in the art, for example, in: V. Hessel and H. Lowe, "Mikroverfahrenstechnik: Komponenten, Anlagen-konzeption, Anwenderakzeptanz", Chem. Ing. Techn. 74, 2002, pages 17-30, 185-207 and 381-400. S. Lobbecke et al., "The Potential of Microreactors for the Synthesis of Energetic Materials", 31$^{st}$ Int. Annu. Conf. ICT; Energetic Materials-Analysis, Diagnostics and Testing, 33, 27-30 Jun. 2000, Karlsruhe, Germany. Microreactors, micromixers, micro-heat-exchangers have been developed, for example in Germany (i.e.: IMM, Mainz, and Forschungszentrum Karlsruhe) and in the USA (i.e.: MIT and DuPont).

An advantage of using a micro- or millireactor is that they have very effective heat transfer to and from the reactor, allowing good control of a highly exothermic reaction. Also the volumes of reagents and products are low, meaning that safety is improved because any explosion is only on a small scale.

In one embodiment, the process steps (c), i.e. the conversion of compound (5) into compound (2), and (d), i.e. the conversion of compound (6) into compound (3), are conducted in continuous mode, in particular these steps are performed in a continuous stirred tank reactor, a microreactor or a millreactor, and the subsequent product stream are mixed in a further microreactor or millireactor, in which the conversion of compounds of formulae (2) and (3) into the compound of formula (4) proceeds. The mixing can be carried out using a conventional mixer, preferably a conventional stirrer or a static mixer such as a T-mixer.

A brief description of the FIGURES is given below.

FIG. 1: set-up for production of pentenoate (1) with $R_1$=tert. butyl and $R_2$=$R_3$=$R_4$=H including flow rates of the pumps as well as the inner diameter of the tubes.

The invention is exemplified in the following Examples.

EXAMPLES

Example 1

Continuous Synthesis of Acrolein from Glycerol

In a continuous stirred tank reactor are placed 14 g glycerol, 40 g KHSO$_4$ and 8 g K$_2$SO$_4$. The mixture is heated up to 200-230° C. Then, during continuous operation, glycerol is added over 90 min at a rate of 380 µL/min. During the addition of glycerol, acrolein and water were distilled off at a constant rate of 390 µl/min such has to keep the volume within the stirred tank reactor constant with 1 ml. During 90 min 35.1 ml were distilled. The distillate consisted of water and acrolein.

Example 2

Continuous Synthesis of Acrolein from Glycerol

In a continuous stirred tank reactor are placed 28 g glycerol, 80 g KHSO$_4$ and 16 g KHSO$_4$. The mixture is heated up to 200-230° C. Then, during continuous operation, glycerol is added over 300 min at a rate of 1600 µL/min. During the addition of glycerol, acrolein and water were distilled off at a constant rate of 1230 µl/min. During 300 min 365 ml were distilled. The distillate consisted of water and acrolein.

Example 3

Continuous Generation of a Compound (1) with $R_1$=tert. butyl and $R_2$=$R_3$=$R_4$=H In a set-up as depicted in FIG. 1 the indicated process flows of the indicated compositions are reacted to form compound (1). with $R_1$=tert. butyl and $R_2$=$R_3$=$R_4$=H. in a crude yield (based on tert-butylacetate) of 82% and a purity (determined by 1H-NMR, pyridine as internal standard) of 86%, indicating a yield of pure product of 71%.

The invention claimed is:
1. A process for preparing a compound of formula (1)

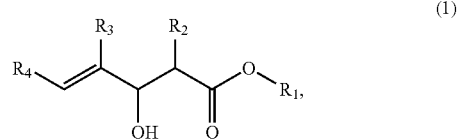

wherein $R_1$ is independently chosen from $C_1$-$C_6$ alkyl, cycloalkyl, aralkyl and aryl, and $R_2$, $R_3$ and $R_4$ are independently chosen from hydrogen and $C_1$-$C_6$ alkyl, cycloalkyl, aralkyl and aryl;

which process comprises the steps of:

a) contacting a compound of formula (2)

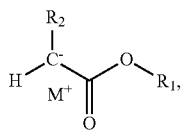
(2)

wherein $R_1$ and $R_2$ are as above and $M^+$ is a monovalent metal ion, with a compound of formula (3)

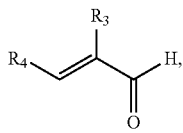
(3)

wherein $R_3$ and $R_4$ are as above, to form a compound of formula (4)

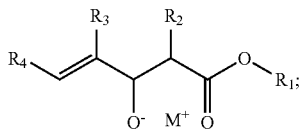
(4)

and b) followed by contacting the compound of formula (4) with an acid to give a compound of formula (1), wherein step (a) and/or step (b) are conducted in continuous mode.

2. The process according to claim 1, wherein the compound of formula (2) is formed by the step of (c) contacting a compound of formula (5)

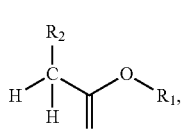
(5)

with a base.

3. The process according to claim 2, wherein step (c) is conducted in continuous mode.

4. The process according to claim 1, wherein the compound of formula (3) is formed by the step of:

(d) dehydration of a compound of formula (6)

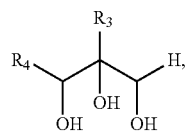
(6)

in the presence of an acid catalyst.

5. The process according to claim 4, wherein step (d) is conducted in continuous mode.

6. A process for preparing the compound of formula (2)

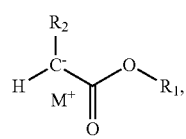
(2)

wherein $R_1$ is independently chosen from $C_1$-$C_6$ alkyl, cycloalkyl, aralkyl and aryl, and $R_2$ is independently chosen from hydrogen and $C_1$-$C_6$ alkyl, cycloalkyl, aralkyl and aryl; and wherein the process comprises the step of (a) contacting a compound of formula (5)

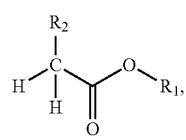
(5)

with a base, wherein the base is lithium diisopropyl amide formed in situ from diisopropyl amine and n-butyl lithium, and wherein step (a) is conducted in continuous mode.

7. The process according to claim 2, wherein the compound of formula (3) is formed by the step of:

(d) dehydration of a compound of formula (6)

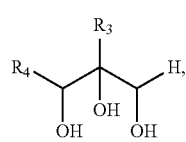
(6)

in the presence of an acid catalyst.

8. The process according to claim 3, wherein the compound of formula (3) is formed by the step of:

(d) dehydration of a compound of formula (6)

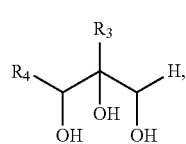
(6)

in the presence of an acid catalyst.

9. The process according to claim 7, wherein step (d) is conducted in continuous mode.

10. The process according to claim 8, wherein step (d) is conducted in continuous mode.

* * * * *